US012593982B2

(12) United States Patent
    Caizzone et al.

(10) Patent No.: US 12,593,982 B2
(45) Date of Patent: Apr. 7, 2026

(54) EARBUD SENSING SYSTEM AND METHOD EMPLOYING LIGHT STEERING AND SPATIAL DIVERSITY

(71) Applicant: Senbiosys, Neuchâtel (CH)

(72) Inventors: Antonino Caizzone, Milvignes (CH); Assim Boukhayma, Neuchâtel (CH)

(73) Assignee: Senbiosys, Neuchâtel (CH)

( * ) Notice: Subject to any disclaimer, the term of this patent is extended or adjusted under 35 U.S.C. 154(b) by 218 days.

(21) Appl. No.: 17/466,356

(22) Filed: Sep. 3, 2021

(65) Prior Publication Data

US 2022/0061669 A1     Mar. 3, 2022

Related U.S. Application Data

(60) Provisional application No. 63/074,120, filed on Sep. 3, 2020.

(51) Int. Cl.
    *A61B 5/00*          (2006.01)
(52) U.S. Cl.
    CPC .......... *A61B 5/0059* (2013.01); *A61B 5/6817* (2013.01); *A61B 2562/0233* (2013.01); *A61B 2562/04* (2013.01)
(58) Field of Classification Search
    CPC . A61B 5/0059; A61B 5/6817; A61B 2562/04; A61B 2562/0233; A61B 5/6804; A61B 5/02411; A61B 5/0205; A61B 5/1115; A61B 5/1118
    See application file for complete search history.

(56) References Cited

U.S. PATENT DOCUMENTS

| | | | |
|---|---|---|---|
| 10,687,717 B1 | 6/2020 | Peterson et al. | |
| 2016/0026212 A1* | 1/2016 | Lee ...................... | G06F 1/3231 |
| | | | 361/679.03 |
| 2016/0085302 A1* | 3/2016 | Publicover ........... | G02B 27/017 |
| | | | 345/633 |
| 2017/0164848 A1* | 6/2017 | Nadeau .............. | A61B 5/14552 |
| 2017/0188851 A1* | 7/2017 | LeBoeuf ............ | A61B 5/02433 |
| 2017/0281087 A1* | 10/2017 | Workman ................ | A61B 8/02 |
| 2018/0014737 A1* | 1/2018 | Paulussen .......... | A61B 5/02416 |
| 2018/0310822 A1* | 11/2018 | Indorf .................. | A61B 5/7405 |
| 2018/0333244 A1* | 11/2018 | Hanks .................. | A61B 5/7278 |
| 2019/0015000 A1* | 1/2019 | Han ...................... | A61B 5/681 |
| 2019/0030230 A1* | 1/2019 | Connor .................. | A61B 5/026 |

(Continued)

FOREIGN PATENT DOCUMENTS

WO      WO 2019198991 A1     10/2019

OTHER PUBLICATIONS

Webster, J.G., "Design of Pulse Oximeters," Bristol. PA: Philadelphia: Institute of Physics Pub., 1-256 (1997).

(Continued)

*Primary Examiner* — Amanda L Steinberg

(74) *Attorney, Agent, or Firm* — HoustonHogle LLP

(57) ABSTRACT

A biomedical sensing module and system employs light steering and sensor spatial diversity to enhance the quality and reliability of its measurements. This is particularly relevant to earbuds. Indeed, unlike in a smartwatch, an earbud-based biomedical sensing system suffers from person-to-person physiological differences at the level of the ear canal. This makes it very complicated to engineer a biomedical platform fitting everybody's differences in ear anatomy.

27 Claims, 9 Drawing Sheets

(56) References Cited

U.S. PATENT DOCUMENTS

| | | | |
|---|---|---|---|
| 2019/0086316 A1 | 3/2019 | Rice et al. | |
| 2019/0365231 A1* | 12/2019 | Kwon | A61B 5/681 |
| 2019/0387972 A1* | 12/2019 | Hu | A61B 5/7214 |
| 2021/0007617 A1 | 1/2021 | Kim et al. | |

OTHER PUBLICATIONS

International Preliminary Report on Patentability Received for International Application No. PCT/IB2021/058073 mailed on Mar. 16, 2023, 7 Pages.

International Search Report and Written Opinion of the International Searching Authority, mailed on Dec. 1, 2021, from International Application No. PCT/IB2021058073, filed on Sep. 3, 2021. 13 pages.

Caizzone, A. "An ultra low-noise micropower PPG sensor," EPFL PhD Thesis (2020).

Tur, E., et al. "Basal perfusion of the cutaneous microcirculation: Measurements as a function of anatomic position," Journal of Investigative Dermatology, 81(15): 442-446 (1983).

Zhang, Y., et al., "Motion artifact reduction for wrist-worn photoplethysmograph sensors based on different wavelengths," Sensors, 19(13): 2019.

Poh, M., et al., "Motion-tolerant magnetic earring sensor and wireless earpiece for wearable photoplethysmography," IEEE Transactions on Information Technology in Biomedicine, 14(13): 786-794 (2010).

* cited by examiner

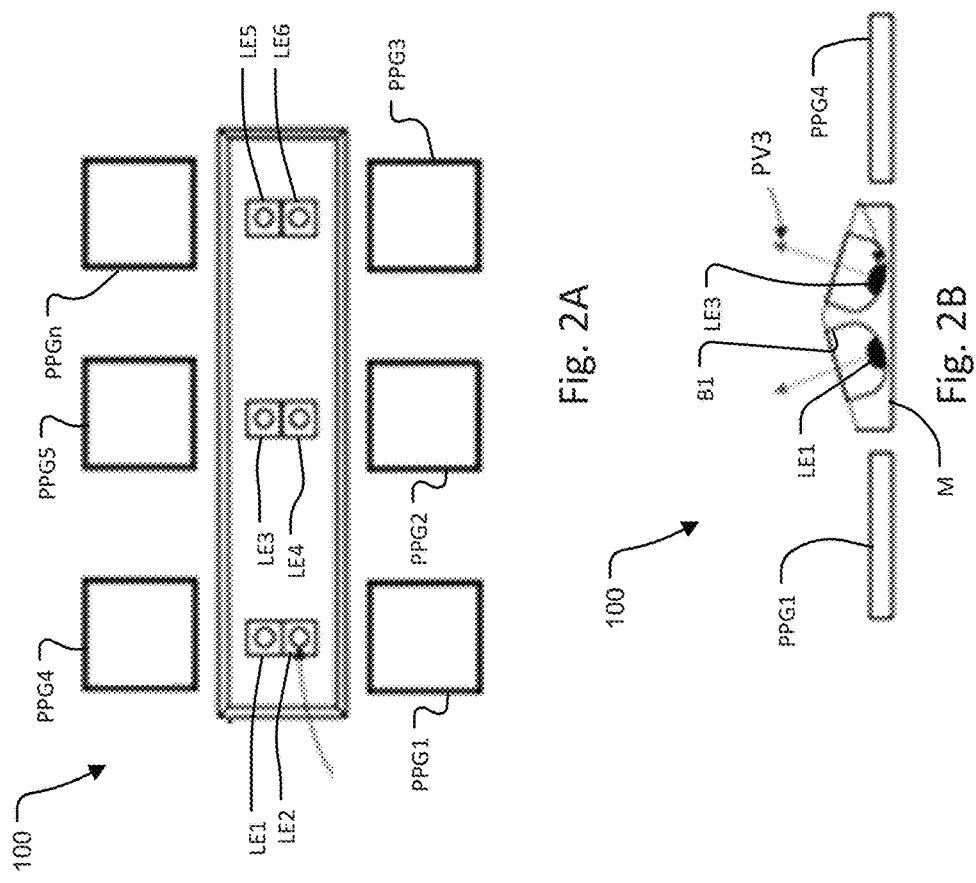
Fig. 2A
Fig. 2B
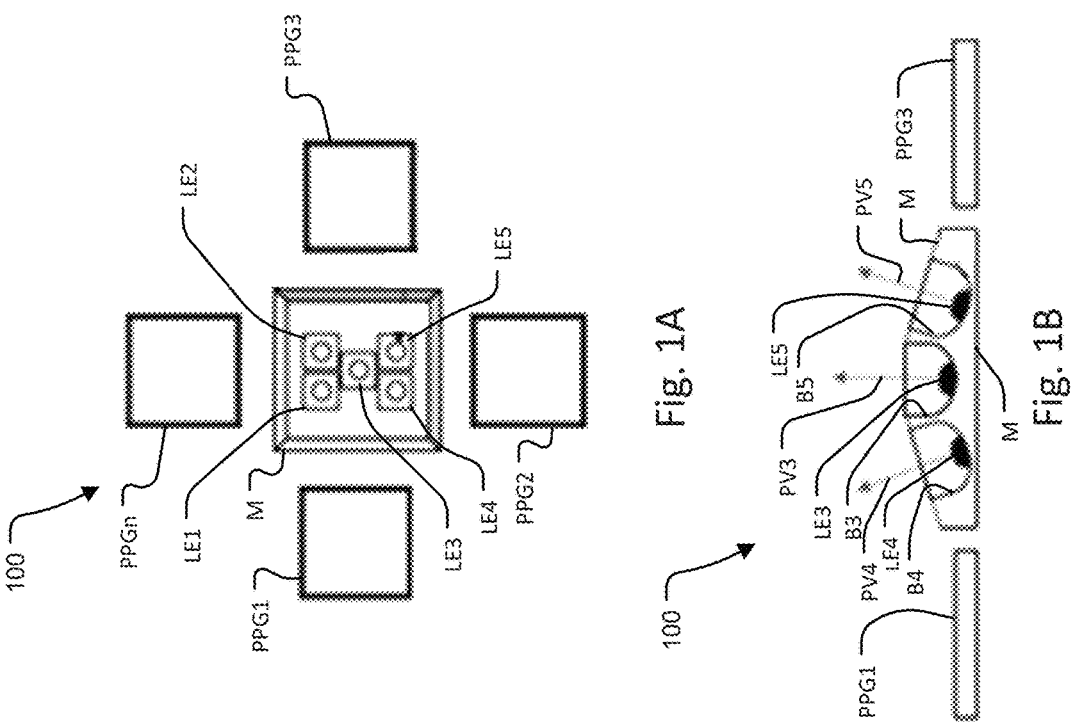
Fig. 1A
Fig. 1B

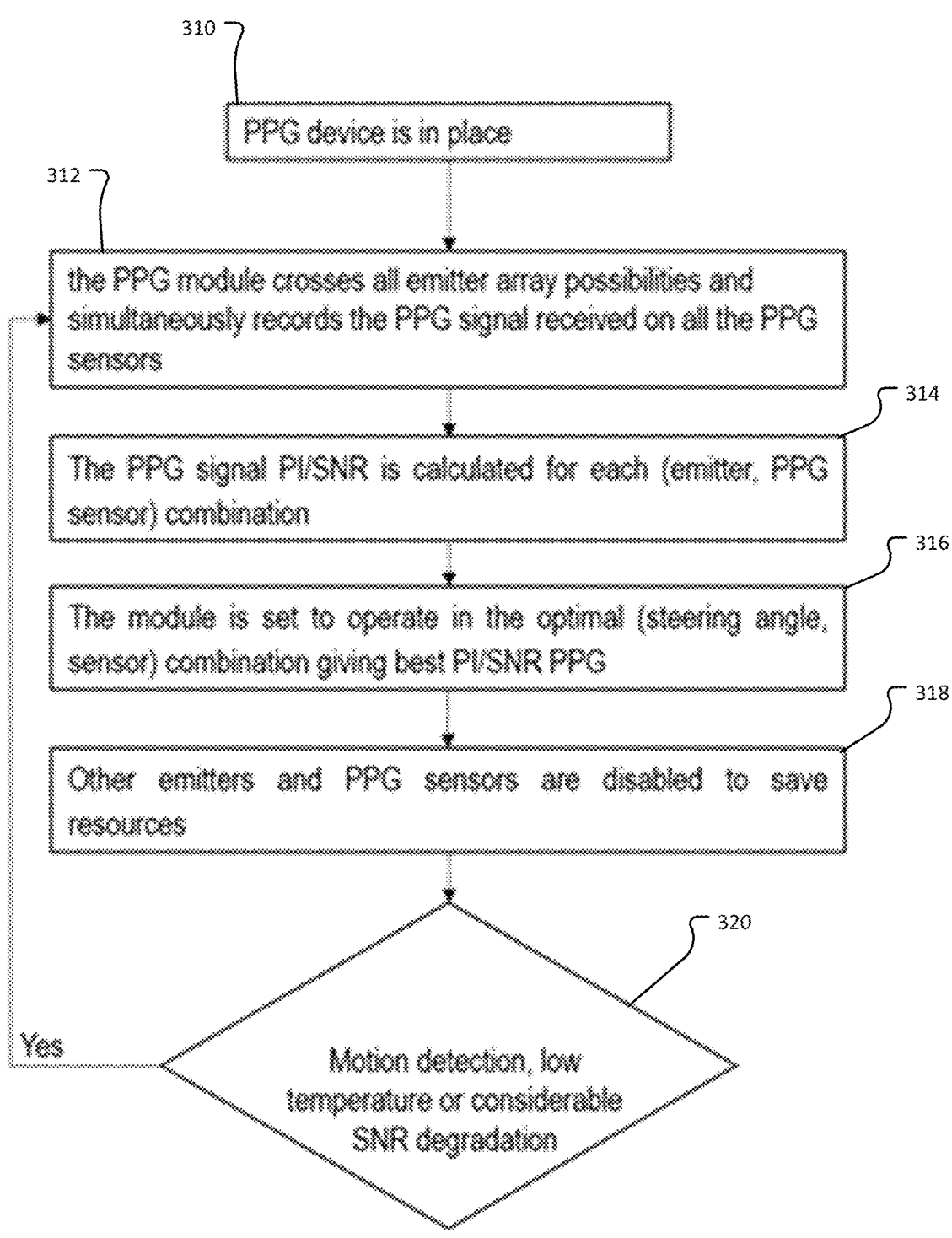

310

PPG device is in place

312 the PPG module crosses all emitter array possibilities and simultaneously records the PPG signal received on all the PPG sensors

314

The PPG signal PI/SNR is calculated for each (emitter, PPG sensor) combination

316

The module is set to operate in the optimal (steering angle, sensor) combination giving best PI/SNR PPG

318

Other emitters and PPG sensors are disabled to save resources

320

Motion detection, low temperature or considerable SNR degradation

Yes

Fig. 3

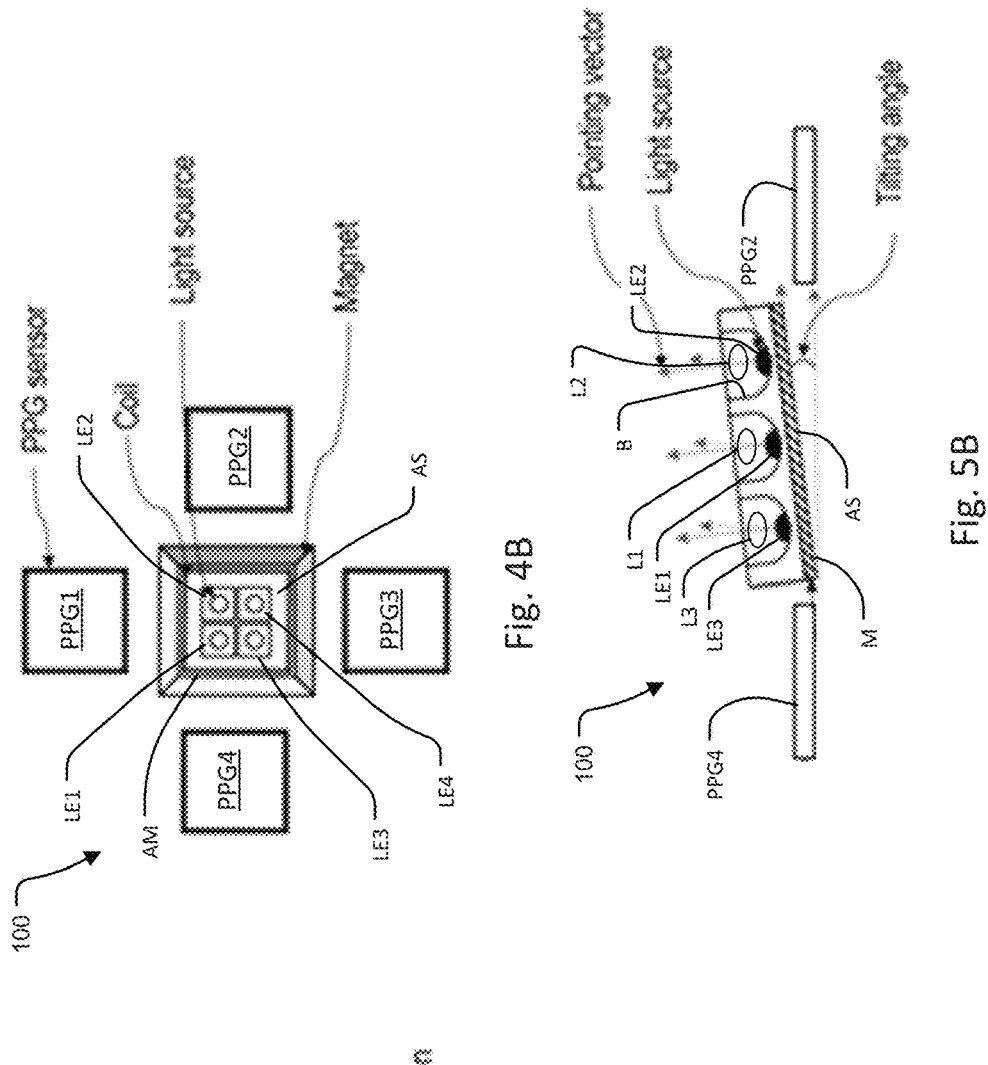
Fig. 4A
Fig. 4B
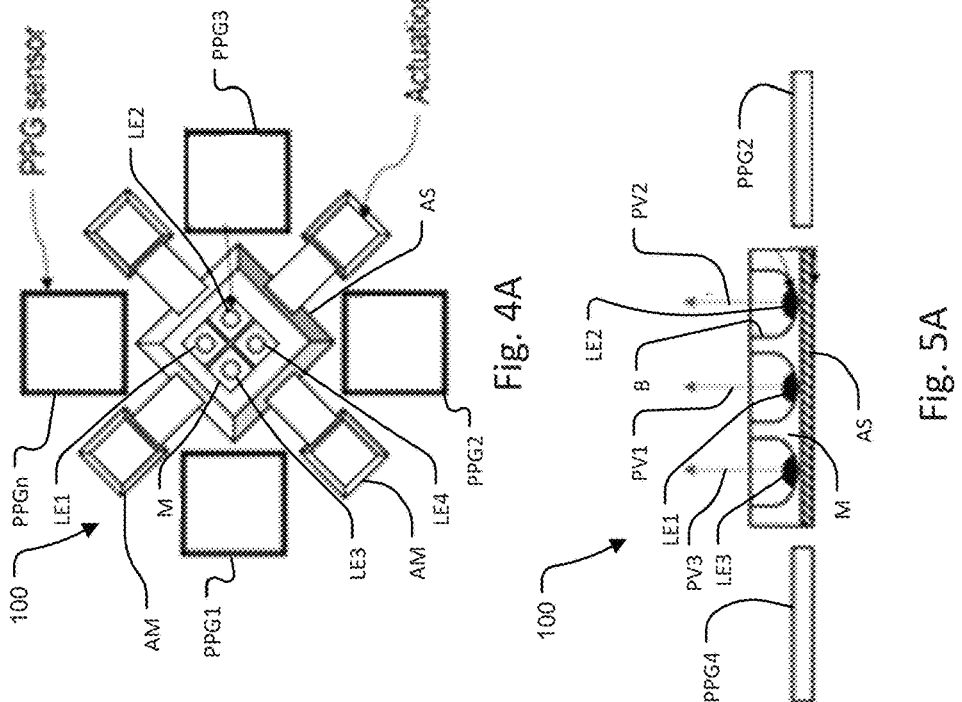
Fig. 5A
Fig. 5B

EARBUD SENSING SYSTEM AND METHOD EMPLOYING LIGHT STEERING AND SPATIAL DIVERSITY

RELATED APPLICATIONS

This application claims the benefit under 35 USC 119(e) of U.S. Provisional Application No. 63/074,120, filed on Sep. 3, 2020, which is incorporated herein by reference in its entirety.

BACKGROUND OF THE INVENTION

Nowadays, the combination of wearable devices and optical heart rate sensors is becoming common. Indeed, few fitness trackers or smartwatches are sold today without an optical heart rate sensor.

The technology behind these sensors is called photoplethysmography (PPG), which is an optical measurement technique used to detect blood volume changes in living tissues. A PPG sensor requires few optoelectronics components, such as a light source, e.g. light-emitting-diode (LED) or VCSEL (Vertical-Cavity Surface-Emitting-Laser) to illuminate the living tissue, a photodetector (PD) to track any light intensity variation due to the blood volume change and an analog front-end (AFE) for signal conditioning and processing.

The importance of PPG for medical monitoring is proven by the number of primary vital signs directly or indirectly recordable out of it, such as the heart rate (HR), the oxygen saturation (SpO2), the breathing rate (BR) and/or the blood pressure (BP).

A PPG signal is obtained by shining light from a LED at a given wavelength, in the visible or near-infrared range, into a human tissue, e.g. finger, forehead, ear lobe or ear canal. A photodetector detects the light transmitted through (transmissive PPG) or reflected from (reflective PPG) the tissue and transforms it into a photogenerated current. The detected signal, i.e. PPG, includes two different components: a large DC (quasi-static) component corresponding to the light diffusion through tissues and nonpulsatile blood layers, and a small AC (pulsatile) part due to the diffusion through the arterial blood. The AC component is only a very small fraction (typically 0.2% to 2%) of the DC one, meaning the AC component is 500 to 50 times smaller than the DC component, respectively. This mostly depends on the body location, the temperature, the LED wavelength and weakly on the skin tone. Such small AC/DC ratio is often called perfusion-index (PI) and ultimately sets one of the limiting challenges for any PPG readout system. Indeed, the AC component carries most of the biomedical information. Low PI values lead to reduced signals fidelity, complicated signal processing schemes and increased power consumption.

The (sensing) body location of the PPG sensor affects the PI and the signal quality. Different measurement sites have been explored, including the wrist, the finger and the ear region (both the lobe and the canal). Generally speaking, the ear has been shown to be among the best locations in terms of PI, at a given optical power, opening up to better biomedical sensing.

In addition to the intrinsically larger PI, the ear comes with the advantage of stable temperature operations and proximity to the heart. The former translates into larger perfusion values, so better PI, while the latter into better pulse wave analysis, thanks to the shorter propagation of the (cardiac) pressure waves.

Another important challenge during a PPG monitoring comes from motion artifacts (MA). MA can be of various types and ultimately distort the PPG signal, MA can be periodic or non-periodic and can present a much larger amplitude than the AC component of the PPG signal. In addition, the MA can fall within the same frequency band as the HR. For these reasons, MA need to be minimized as much as possible. In this regard, the ear exhibits yet another advantage. Indeed, it tends to show less MA than other locations due to the lower extent of motion happening in the head with respect to the limbs. More specifically, in the ear canal (particularly the inner one), physiognomy can be particularly helpful to reduce drastically the MA, thanks to the combination of bony and cartilaginous anatomic regions.

SUMMARY OF THE INVENTION

This invention concerns a biomedical sensing module and system that takes advantage of the light steering and sensor spatial diversity to enhance the quality and the reliability of the measurements. This is especially relevant to earbuds. Indeed, unlike in a smartwatch, an earbud-based biomedical sensing system suffers from person-to-person physiological differences at the level of the ear canal. This makes it very complicated to engineer, in the ear, a biomedical platform fitting different anatomies.

This invention can improve the performance of photoplethysmographic (PPG) sensing at the ear or other areas with optimum power consumption, high fidelity and is much less affected by the ear canal anatomical variations. A PPG sensor has been proven to carry information about vital signs such as the heart rate (HR), its variability (HRV), the oxygen saturation (SpO2), the breathing rate (BR) and the blood pressure (BP).

In examples, multi-PPG sensors are distributed around a light source to exploit spatial diversity (or distribution) and create different PPG channels. The redundancy of such set-up can effectively reduce the impact of MA and reduce the effect of badly placed PPG sensors. This is particularly important in the ear due to the person-to-person physiological differences at the level of the ear (particularly in the canal dimensions). The advantages of the sensor spatial diversity can be enhanced if accompanied by a dynamic lighting scheme.

Light steering, either passive or active, is extensively used nowadays in many applications such as optical networks, projection displays, LIDAR. (light detection and ranging) and 3D printing. The great development of the MEMS (Micro-Electro-Mechanical-Systems) technology makes the light steering particularly reliable and cost-effective. Indeed, thanks to the proliferation of lasers in many applications, the MEMS technology has been extensively used to deflect laser beams in both static and dynamic operations: the so-called MEMS mirror steering.

A PPG sensor can considerably benefit from a light source steering mechanism. Unlike the MEMS mirror steering, in the PPG case the steering happens by geometrical considerations (passive) or by actuating the surface underneath the light source (active), leading into a pointing vector or optical axis deviation.

As above mentioned, the sensor spatial diversity is key to reduce the impact of MA and reduce the effect of badly placed PPG sensors. A light source steering, either passive or active, could considerably reduce those challenges and particularly the one related to poor sensor position, which is particularly important in the ear, due to the large physiognomy variations. Merging the sensor spatial diversity with the light steering leads to high fidelity PPG signals and low power operations.

Similarly to the MEMS mirror steering, different actuation schemes are possible including the electrostatic, the piezoelectric, and the electromagnetic. A passive scheme is also possible.

Combining light steering with sensing spatial diversity in PPG modules paves the path for several improvements including:

Better PPG signal fidelity and more resilience to MA,

Lower power,

Adaptation to ear physiognomy.

Given the large person-to-person ear physiognomy variation, the embodiment proposed in this invention does not need any user intervention to find a good sensing spot. This can lead to better signal extraction and/or reduce LED power consumption. Indeed, once a good sensing spot is found, less lighting power is often needed to operate the sensor.

The industrial applications relate to the earbud consumer electronic devices. This is an emerging market which is just showing a small fraction of its future potential. This is particularly true in specific growing use cases such as sleep monitoring. The proposed embodiment and method are particularly interesting in this space, due to challenges resulting from effectively measuring a PPG signal in the ear, during sleep.

This invention is also of direct interest to hearing aid providers, that look at adding biomedical sensing to complement their current devices. Specifically, hearing aids are getting smaller and smaller with the ultimate goal to be hidden completely in the deep ear canal. This may result in physiological challenges to get a good PPG signal.

In general, according to one aspect, the invention features a sensor module comprising an array of light emitters, an array of optical sensors, and a control unit for using different combinations of the light emitters and optical sensors to monitor vital signs of a user.

In embodiments, the light emitters and/or the optical sensors are directed in different directions.

Also, the light emitters and/or the optical sensors can be directed in different directions under the control of the control unit.

In some examples, the array of optical sensors is arranged around the array of light emitters.

In other examples, the array of light emitters is arranged around the array of optical sensors.

An active steering mechanism can be used for steering pointing vectors of the optical sensors and/or the light emitters. Also, the control unit might then control the active steering mechanism for different pointing vectors.

In addition, baffles around the light emitters and/or the optical sensors are helpful in some cases.

In general, according to another aspect, the invention features an earbud comprising a sensor module, including an array of light emitters, an array of optical sensors, and a control unit for using different combinations of the light emitters and optical sensors to monitor vital signs of a user. A battery power supply provides power for the sensor module.

In general, according to another aspect, the invention features a method for configuring an earbud, comprising assessing different combinations of light emitters and optical sensors to monitor vital signs of a user; and using one or more pairs of light emitters and optical sensors to determine the vital signs.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 1A and 1B are a plan view and a schematic side cross sectional view of an exemplary sensor module exploiting passive light steering combined with sensor spatial diversity;

FIGS. 2A and 2B are a plan view and a schematic side cross sectional view of an exemplary sensor module according to a second embodiment;

FIG. 3 is a flow diagram showing the proposed PPG module's workflow or method of operation for passive light steering;

FIGS. 4A and 4B are plan views of two possible module embodiments exploiting active light steering;

FIGS. 5A and 5B are schematic side cross sectional views showing the tilting of the light emitters LE in their mold M by an active steering mechanism;

Figures 2C, 2D:
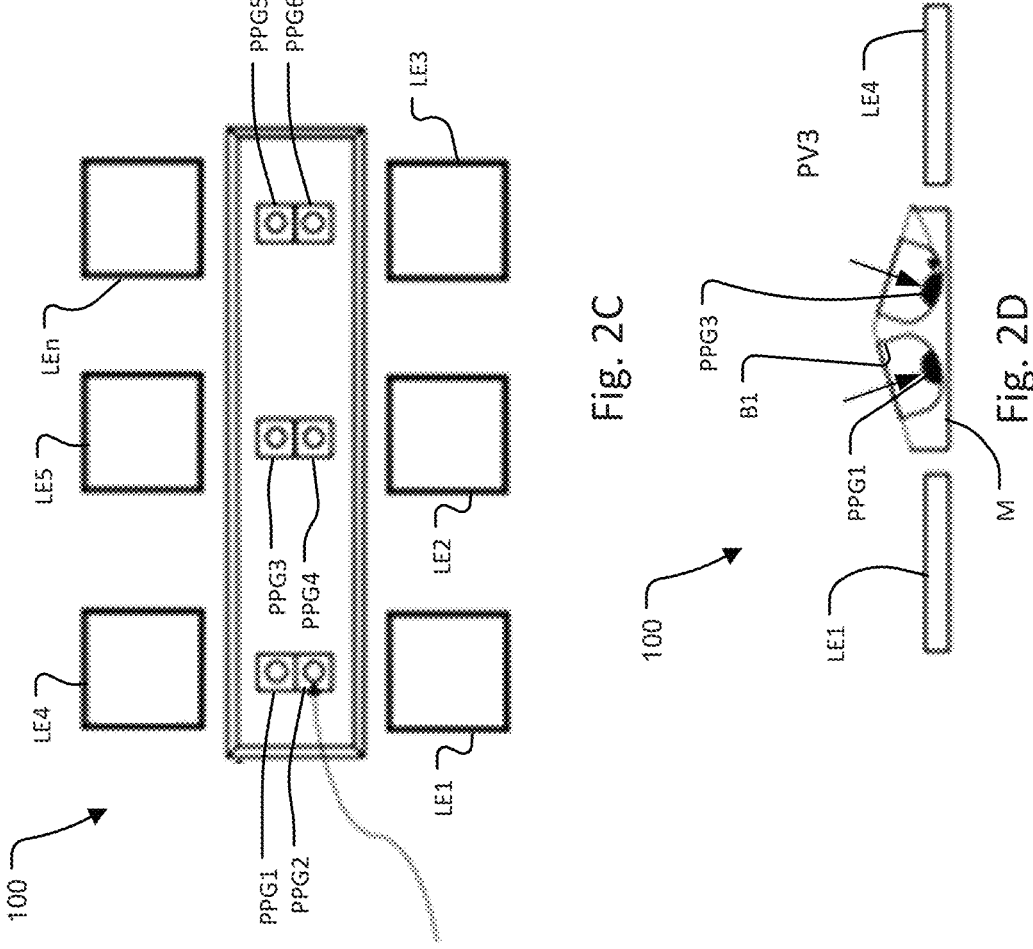
FIGS. 2C and 2D are a plan view and a schematic side cross sectional view of an another exemplary sensor module according to another embodiment.

DETAILED DESCRIPTION OF THE
PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The preferred embodiment of the PPG module preferably comprises one or more of the following features:

a plurality of light sensors PPG1-$n$ (designed for PPG signal requirements) spatially distributed to capture light from different angles and different locations and thus cope with a variety of ears' dimensions;

a light source LE that can emit in different directions;

a control unit (CU) that controls the light source angular direction (light steering). The control unit uses the light sensors' output together with the input from other sensors such as motion sensors and/or temperature sensors to find the steering angle optimizing the signal quality or reacting to events such as motion.

In order to optimize the PPG signal quality and light source power consumption, the CU operates the module in the following way:

A. Once the PPG device is in place, the CU crosses all possible emitter steering angles and simultaneously senses the PPG signal received by the multiple spatially distributed PPG channels.

B. The perfusion-index (PI) and the signal-to-noise ratio (SNR) of the PPG signal is calculated for each angle and on each sensor.

C. The CU activates the combination of the steering angle and the PPG sensor position, i.e. channel, that leads to the best PPG PI/SNR, saving resources and power consumption.

D. If MAs are detected, by the means of a motion sensor, the CU reacts by balancing the MA thanks to a change of steeling or goes back to step A). The same applies in case of low temperature operations, which requires a refined coupling between the light and the sensor.

Such a PPG module can be realized in two main possible strategies, one exploiting passive light steering/detection and the second exploiting active light steering/detection, or a combination of these two strategies.

FIGS. 1A and 1B show an exemplary module 100 exploiting passive light steering combined with sensor spatial diversity. The module embeds a plurality (n=4) of PPG sensors PPG1-PPGn spatially distributed with respect to an array of five light emitters LE1-LEn (n=5) such as in a quadrant or cross pattern. In this embodiment, the light steering happens passively, by the geometrical arrangement of the plurality of light emitters LE as depicted. Specifically, the array of four light emitters is placed on a mold M which ensures no direct (light) crosstalk between the light emitters LE and the sensors PPG and the passive steeling mechanism. Specifically, each light emitter LE is disposed within a respective baffle or light director B formed in the mold. In the example, the baffles are cup-shaped depressions or blind holes formed in the mold or housing M. In some examples, the inner walls of each of the baffles B1 to B5 is coated with a reflective layer such as a thin metal layer or possibly a light absorbing layer such as a black paint or carbon black paint. In addition, each light emitter LE is directed in a different direction characterized by different pointing vectors or optical axes PV. Indeed, by disposing the light sources of the module in a way that each one is pointing at a different angle, the light angular steering can be performed by activating a sub-group and disabling the others. In one example, the angle between different pointing vectors is greater than 5 degrees or even greater than 10 degrees or 20 degrees, such as the angle between pointing vectors PV3 and PV4. The different angles between pointing vectors PV4 and PV5 can be greater than 10 degrees or even greater than 20 degrees or 30 degrees.

In other examples, liquid lens or metalenses or metaoptics are added in front of the light emitters and/or the PPG sensors to improve steering.

FIGS. 2A and 2B show another module 100 exploiting passive light steering combined with sensor spatial diversity. The module embeds a plurality (6) of PPG sensors PPG1-PPGn spatially distributed in two lines above and below with respect to an array of six light emitters LE1-Len arranged in three groups of two. In this embodiment, the light steering also happens passively, by the geometrical arrangement of the plurality of light emitters as depicted.

As shown in FIGS. 2C and 2D, in other embodiments, the location of the PPG sensors PPG1-PPGn and light emitters LE1-LEn can be swapped so that the sensors PPG are directed in different directions, instead of the emitters LE. This exploits the Helmholtz reciprocity principle.

FIG. 3 shows an example of the proposed PPG module's workflow or calibration method of operation in the case of a passive steering configuration implemented by an array of emitters.

In more detail, in step 310, the PPG device 100 is placed in the patient's ear canal.

In step 312, the control unit CU assesses every potential pair or combination of PPG sensor PPG and light emitter LE. Specifically, the control unit CU determines the optical coupling between each individual light emitter LE and every PPG sensor PPG1-PPGn of the device 100.

From this analysis, the control unit calculates the PPG signal and specifically the perfusion index and signal to noise ratio (SNR) for each pair in step 314.

Then, in step 316 the control unit determines the optimum combination of light emitter and PPG sensor or several light emitter PPG sensor pairs that provide the best coupling and specifically perfusion index and signal to noise ratio. Then in step 318, the control unit disables the other emitters and PPG sensors.

The optimal sensor-emitter pair or pairs are then used by the control unit to monitor the user and specifically the user's heart rate (HR), the oxygen saturation (SpO2), breathing rate (BR) and/or the blood pressure (BP) until motion is detected or the ambient temperature changes or there is a determined SNR degradation. Then, in step 320, upon one or more of these events, the calibration sequence is performed again starting with step 312.

FIGS. 4A and 4B show two possible module embodiments exploiting active light steering combined with sensor spatial diversity. In each embodiment, the module 100 embeds a plurality of PPG sensors PPG1-PPG4 spatially distributed with respect to a single or array of light emitters LE1-LE4 disposed on an actuating support AS. Similarly, to the passive mechanism, the array of light emitters is placed on a mold or housing M which ensures no or reduced direct (light) crosstalk between each of the light emitters LE1-LE4 and the sensors PPG1-PPG4. The actuating support AS, which carries the mold M with the light emitters LE, is moved or tilted by the actuator of an active steering mechanism. An active steering mechanism AM allows angular steering of the emitted light by tilting the mold or housing M. In the illustrate embodiment, the active steering mechanism AM is able to tilt the mold M around two orthogonal axes defined by the plane of the drawing.

The actuator AM can be based on different technologies and employ different actuation modalities such as electrostatic or piezoelectric as shown in FIG. 4A, or electromagnetic actuation mechanism AM such as a voice coil as in FIG. 4B.

FIGS. 5A and 5B show the tilting of the light emitters LE in their mold M by the active steering mechanism.

In addition, this embodiment also employs lens based beam steering. Flexible lens L1-L3 are liquid lens or metalenses or metaoptics (metamaterials), in different examples, and provide a single or array of light emitters LE disposed on a focal plane and exploiting the mechanical variation of the lens to achieve different light emitting angles to modulate the pointing vector.

In addition, in other embodiments, the locations of the PPG sensor and light emitters are swapped in FIGS. 4A, 4B, 5A, and 5B as described earlier in connection with FIGS. 2C and 2D.

Figure 6:
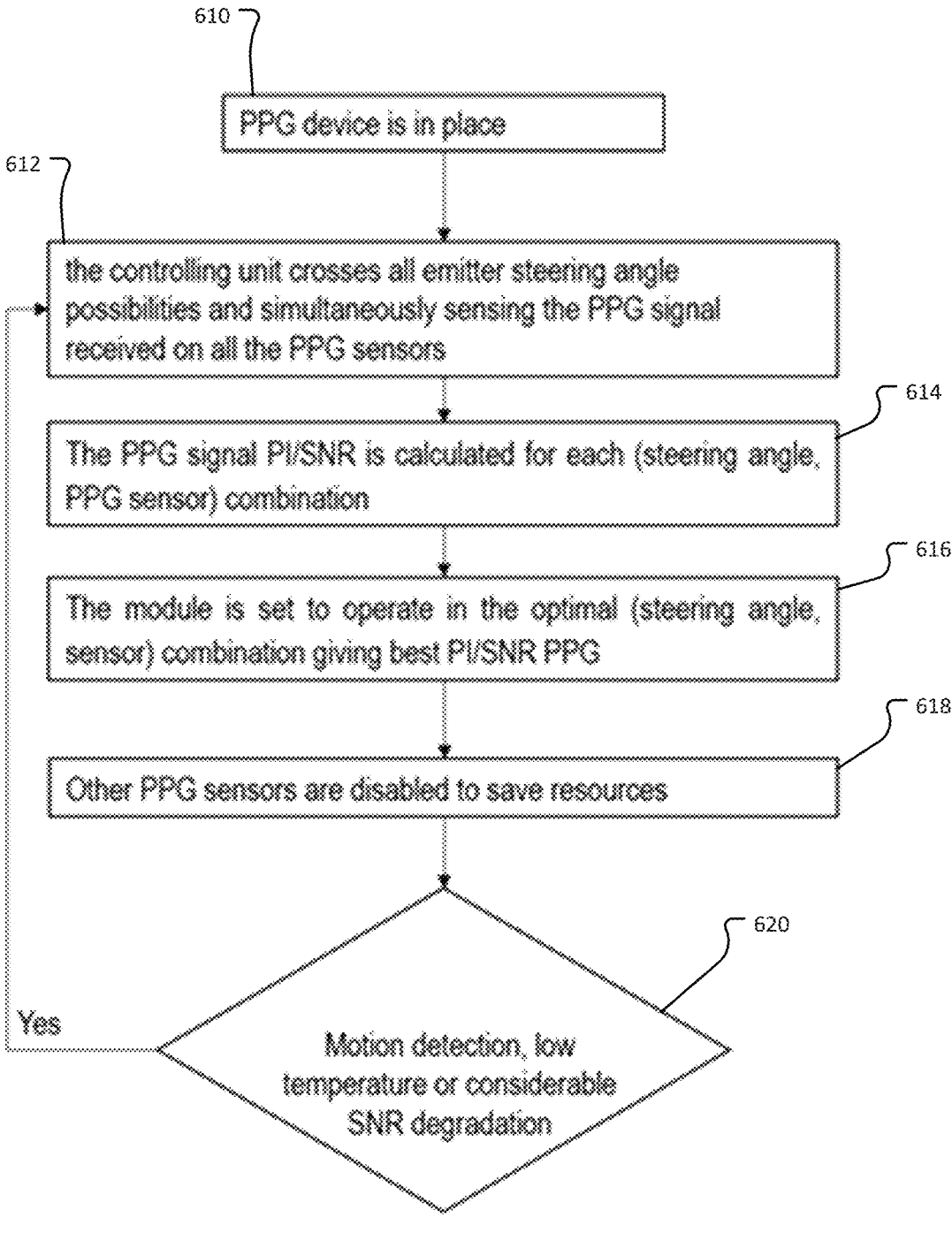
FIG. 6 is a flow diagram showing the proposed PPG module's workflow or method of operation for active steering.
Figures 7A, 7B, 8A, 8B:
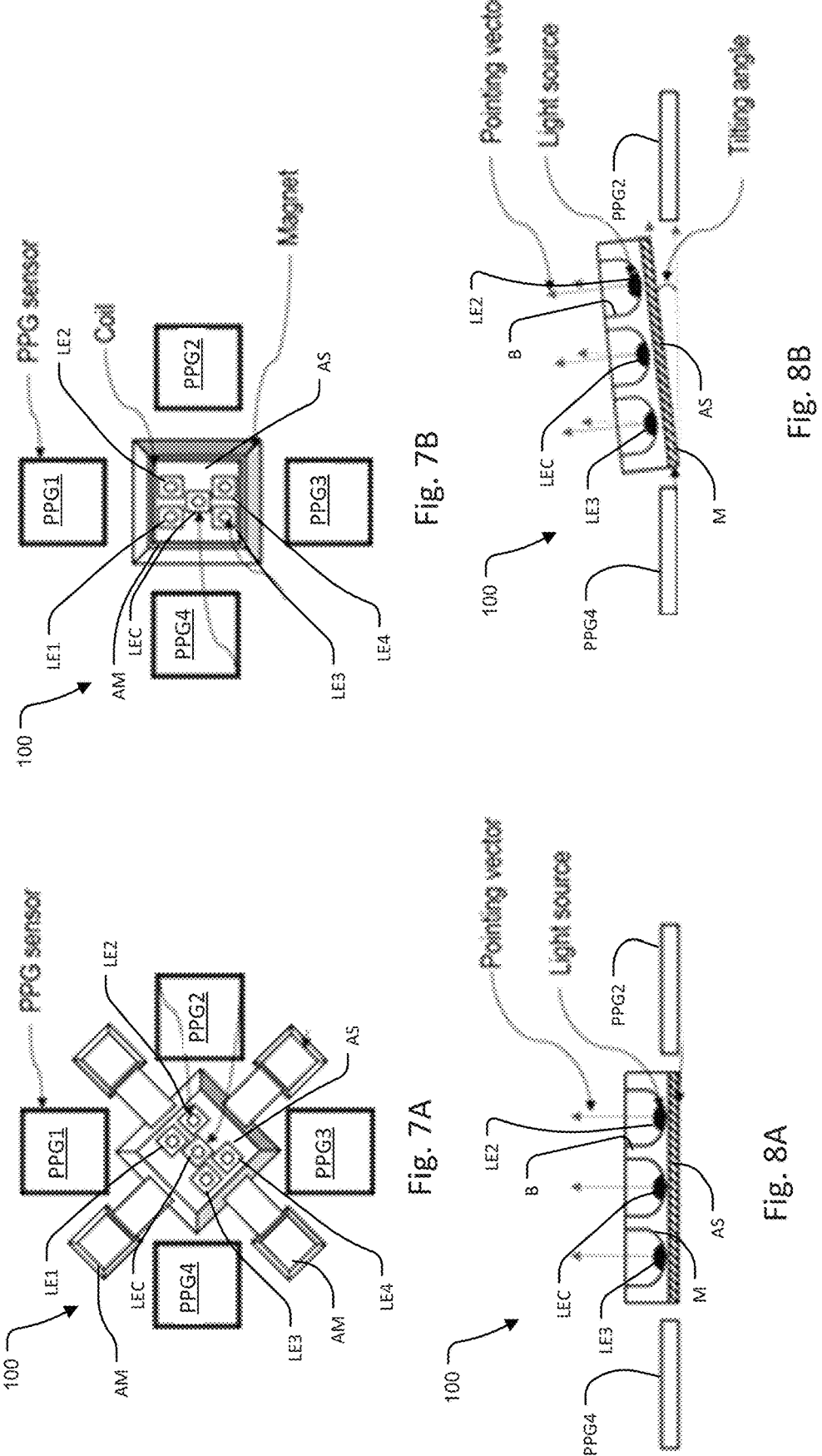
FIGS. 7A and 7B are plan views of two possible module embodiments exploiting active light steering, a central light source, and sensor spatial diversity.
FIGS. 8A and 8B are schematic side cross sectional views showing the tilting of the light emitters LE in their mold M by the active steering mechanism employing the central light source.
Figure 9:
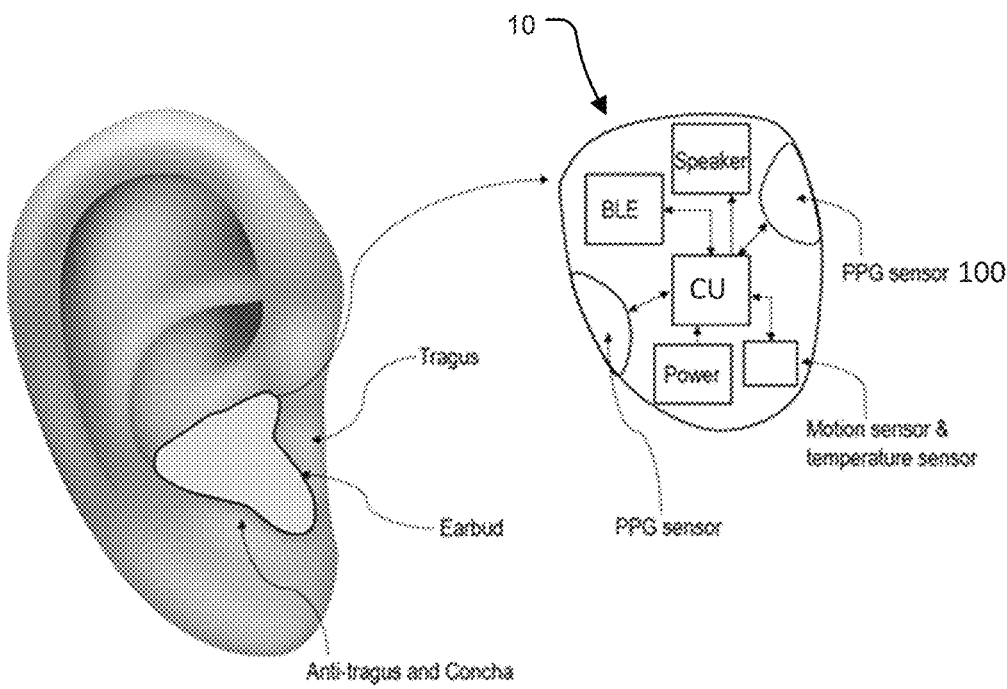
FIG. 9 is a schematic view of an earbud embodiment embedding two PPG sensor modules.
Figure 10:
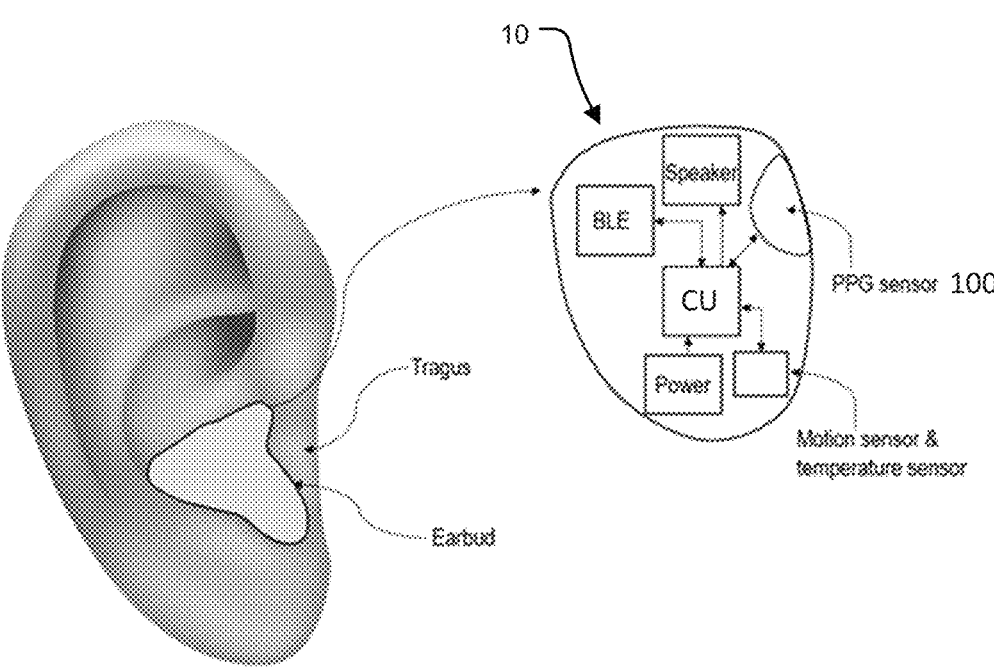
FIG. 10 is a schematic view of an earbud embodiment embedding one PPG sensor module.
Figure 11:
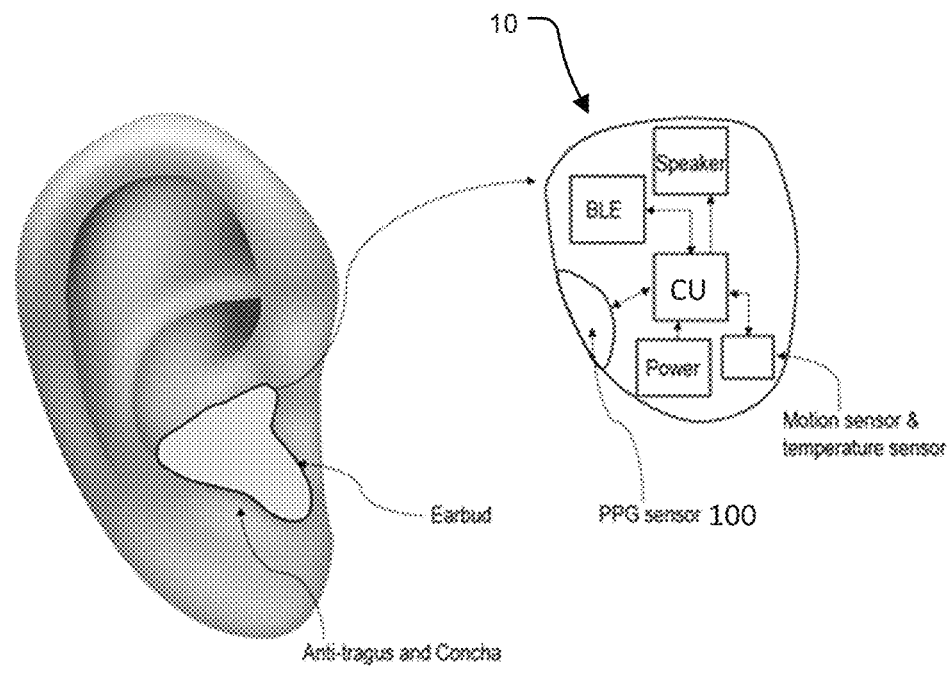
FIG. 11 is a schematic view of an earbud embodiment embedding one PPG sensor module.
Figure 12:
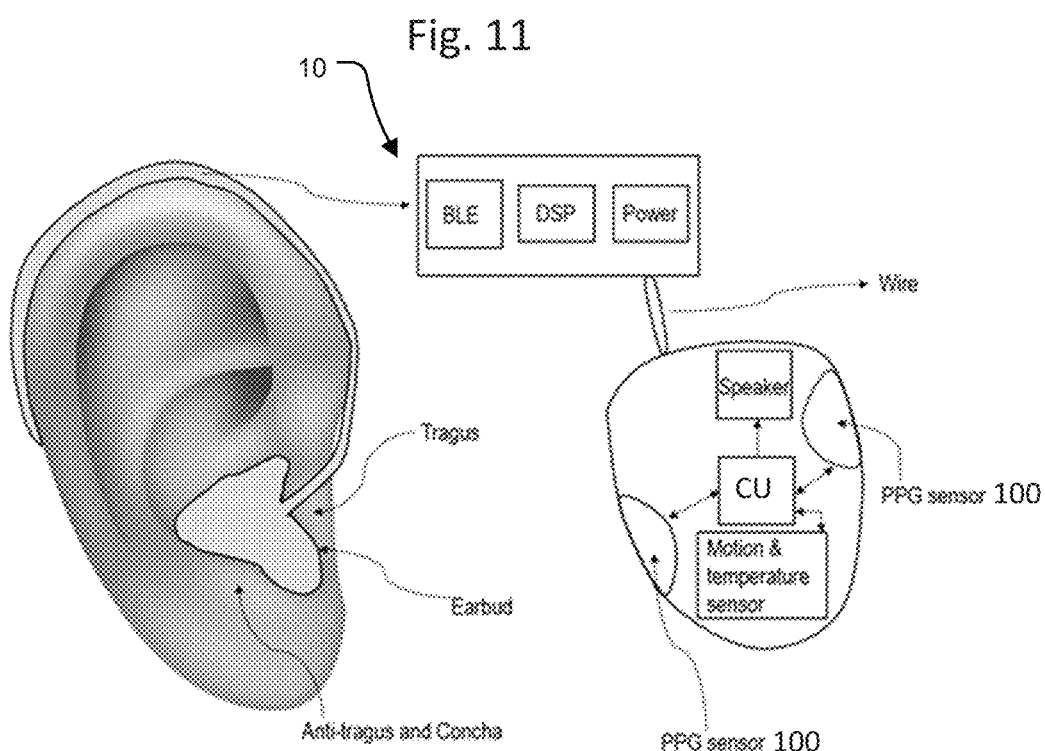
FIG. 12 is a schematic view of an embodiment of an earbud embedding two PPG sensor modules and complemented by a second device, wire connected, behind the ear pinna.
Figure 13:
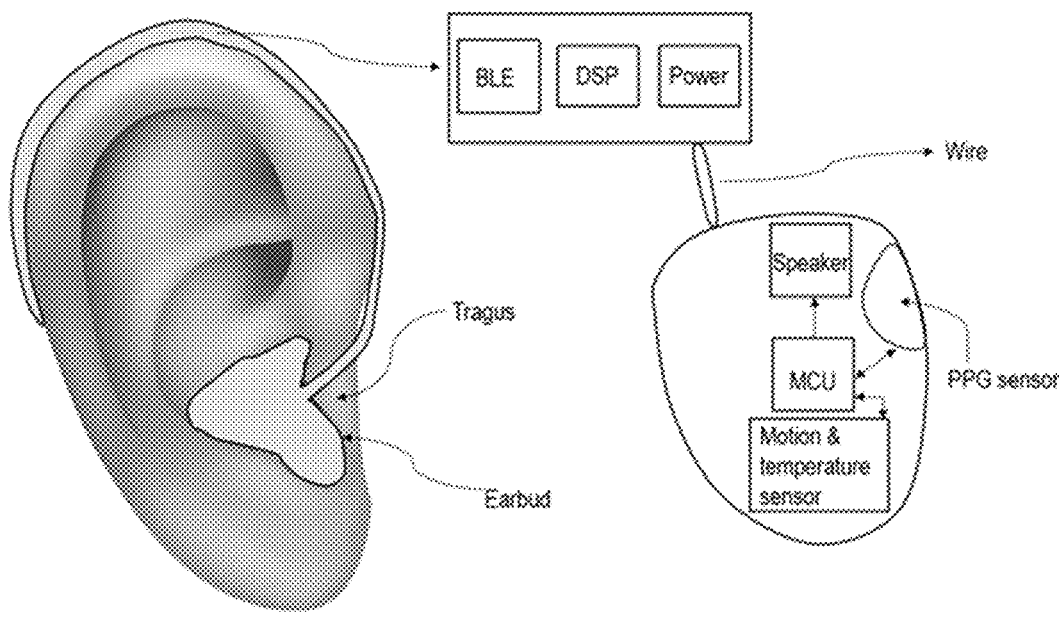
FIG. 13 is a schematic view of an embodiment of an earbud embedding one PPG sensor module and complemented by a second device, wire connected, behind the ear pinna.
Figure 14:
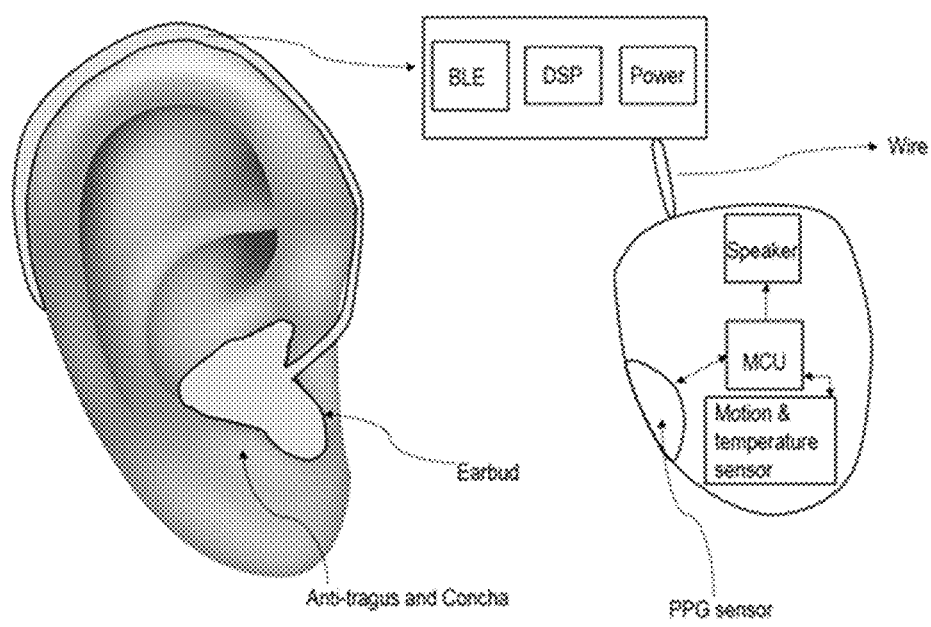
FIG. 14 is a schematic view of an embodiment of an earbud embedding one PPG sensor module and complemented by a second device, wire connected, behind the ear pinna.

FIG. 6 shows an example of the proposed PPG modules workflow in the case of an active steering configuration.

In more detail, in step 610, the PPG device 100 is placed in the patient's ear canal.

In step 612, the control unit CU assesses every potential pair or combination of PPG sensors and light emitters LE for every addressable steering angle for the light emitters and/or sensors. Specifically, the control unit CU determines the optical coupling between each individual light emitter LE and every PPG sensor PPG1-PPGn of the device 100 while controlling the actuator AM to change the steering.

From this analysis, the control unit calculates the PPG signal and specifically the perfusion index and signal to noise ratio (SNR) for each pair and steering angle in step 614.

Then, in step 616 the control unit determines the optimum combination of light emitter and PPG sensor or several light emitter PPG sensor pairs and steering angle that provide the best coupling and specifically perfusion index and signal to noise ratio. Then in step 318, the control unit disables the other emitters and PPG sensors while activating the steering mechanism to the determined best setting.

The optimal sensor-emitter pair or pairs are then used by the control unit to monitor the user and specifically the user's heart rate (HR), the oxygen saturation (SpO2), breathing rate (BR) and/or the blood pressure (BP) until motion is detected or the ambient temperature changes or there is a determined. SNR degradation. Then, in step 620, upon one or more of these events, the calibration sequence is performed again starting with step 612.

FIGS. 7A and 7B and 8A and 8B show other embodiments of PPG device 100 with an active light steering module. In these embodiments, one central light source LEC, emitting in a way that leads to equal signal detection by the PPG sensors when the module is emitting towards a horizontal reflector, is first used. In case the device is in contact with the skin at a given position, a mismatch in the signal received by the detectors appears. This mismatch is used to identify the optimal angular steering.

FIGS. 9-14 show different possible integrations of the described PPG sensor module 100 in an earbud 10. Multiple PPG sensing locations are possible including, but not limited to, the tragus and the anti-tragus & concha ones. The inner ear canal is also possible since the earbud can be engineered such as a hearing aid device. The earbud may have one device only or a combination of them, wire connected. In the former case, the earbud integrates the sensor, the control unit CU, the speaker, the motion and temperature sensor, the Bluetooth low energy (BLE), and the power management unit, including the battery. In the latter case, the earbud integrates the sensing and the control unit CU, while a second device, by preference behind the ear pavilion, integrates the BLE, the power and a digital-signal-processing (DSP) for signal vital sign extraction, including, but not limited to, the HR, HRV, SpO2, BR and BP.

While this invention has been particularly shown and described with references to preferred embodiments thereof, it will be understood by those skilled in the art that various changes in form and details may be made therein without departing from the scope of the invention encompassed by the appended claims.

What is claimed is:

1. A sensor module, comprising:

an array of light emitters;

an array of optical sensors; and a control unit for using different combinations of the light emitters and optical sensors to monitor vital signs of a user, including assessing optical coupling between combinations of the light emitters and the optical sensors by calculating a perfusion index and signal to noise ratio for each pair of light emitters and optical sensors, determining an optimum combination of the light emitters and optical sensors based on the assessed optical coupling, deactivating the light emitters and the optical sensors not in the optimum combination such that only some of the light emitters and the optical sensors are disabled while others remain active, using the optimum combination of the light emitters and optical sensors to monitor the vital signs of the user, and, in response to detection of motion, change in ambient temperature, or a degradation of signal to noise ratio for the optimum combination, re-assessing the optical coupling between the combinations of the light emitters and the optical sensors to determine a new optimum combination;

wherein the light emitters and/or the optical sensors are dynamically directed in different directions, wherein: the array of light emitters comprises a plurality of light emitters oriented in different directions such that the light emitters have different pointing vectors relative to each other, and the array of optical sensors comprises a plurality of optical sensors spatially distributed around the array of light emitters; or the array of optical sensors comprises a plurality of optical sensors oriented in different directions such that the optical sensors have different pointing vectors relative to each other, and the array of light emitters comprises a plurality of light emitters spatially distributed around the array of optical sensors; and wherein: the spatial distribution of the optical sensors around the array of light emitters includes the optical sensors forming a cross pattern around the array of light emitters or forming two lines of optical sensors above and below the array of light emitters; or the spatial distribution of the light emitters around the array of optical sensors includes the light emitters forming a cross pattern around the array of optical sensors or forming two lines of light emitters above and below the array of optical sensors.

2. The sensor module as claimed in claim 1, wherein the light emitters and/or the optical sensors are directed in different directions under the control of the control unit.

3. The sensor module as claimed in claim 1, wherein the array of optical sensors is arranged around the array of light emitters.

4. The sensor module as claimed in claim 1, wherein the array of light emitters is arranged around the array of optical sensors.

5. The sensor module as claimed in claim 1, further comprising an active steering mechanism for steering pointing vectors of the optical sensors and/or the light emitters.

6. The sensor module as claimed in claim 5, wherein the control unit controls the active steering mechanism for different pointing vectors.

7. The sensor module as claimed in claim 5, wherein the control module assessing the optical coupling between the combinations of the light emitters and the optical sensors includes assessing every potential coupling between each light emitter of the array of light emitters and each optical sensor of the array of optical sensors at every addressable steering angle for the light emitters and/or the optical sensors, and the optimum combination comprises an optimum steering angle.

8. The sensor module as claimed in claim 1, further comprising baffles around the light emitters and/or the optical sensors.

9. The sensor module as claimed in claim 1, wherein the control unit assesses optical coupling by determining a perfusion index for combinations of the light emitters and the optical sensors.

10. The sensor module as claimed in claim 1, wherein the control unit assesses optical coupling by determining signal and noise for combinations of the light emitters and the optical sensors.

11. The sensor module as claimed in claim 1, further comprising a motion sensor for determining motion of the sensor module.

12. The sensor module as claimed in claim 11, wherein the control unit monitors the motion sensor and again assesses optical coupling between combinations of the light emitters and the optical sensors based on detected motion, and deactivating the light emitters and the optical sensors based on the assessed optical coupling such that only some of the light emitters and the optical sensors are disabled while others remain active.

13. The sensor module as claimed in claim 1, further comprising a temperature sensor for determining ambient temperature.

14. The sensor module as claimed in claim 13, wherein the control unit monitors the temperature sensor and again determines optical coupling between combinations of the light emitters and the optical sensors based on detected temperature.

15. The sensor module as claimed in claim 1, wherein the sensor module is located in an ear canal of a user.

16. The sensor module as claimed in claim 1, further comprising a mold, wherein the array of light emitters are in the mold and the array of optical sensors are in the mold.

17. The sensor module as claimed in claim 16, further comprising baffles formed in the mold around the light emitters and/or the optical sensors to reduce crosstalk.

18. The sensor module of claim 17, wherein the baffles are cup-shaped depressions or blind holes formed in the mold.

19. The sensor module of claim 18, wherein an inner wall of each of the baffles is coated with a reflective layer or a light absorbing layer.

20. The sensor module as claimed in claim 1, further comprising an actuating support on which the light emitters and/or the optical sensors are mounted, wherein the actuating support is moved and/or tilted under control of the control unit in order to dynamically direct the light emitters and/or the optical sensors in different directions.

21. The sensor module as claimed in claim 1, further comprising flexible lenses to achieve different light emitting angles in order to dynamically direct the light emitters in different directions.

22. The sensor module as claimed in claim 1, wherein each pair of light emitters and optical sensors for which the optical coupling is assessed comprises one light emitter of the array of light emitters and one optical sensor of the array of optical sensors, and the determined optimum combination that is used to monitor the vital signs of the user is one of the pairs of light emitters and optical sensors for which the optical coupling is assessed.

23. The sensor module as claimed in claim 1, wherein a pointing vector of a given light emitter or optical sensor refers to a central optical axis of emission or detection extending normal to an emitting or sensing surface of the given light emitter or optical sensor.

24. The sensor module as claimed in claim 1, wherein the pointing vectors of the light emitters or optical sensors differ from each other by at least five degrees.

25. The sensor module as claimed in claim 1, wherein the control module assessing the optical coupling between the combinations of the light emitters and the optical sensors includes assessing every potential coupling between each light emitter of the array of light emitters and each optical sensor of the array of optical sensors.

26. An earbud, comprising:
a sensor module, including an array of light emitters, an array of optical sensors, and a control unit for using different combinations of the light emitters and optical sensors to monitor vital signs of a user by assessing optical coupling between combinations of the light emitters and the optical sensors and deactivating the light emitters and the optical sensors based on the assessed optical coupling such that only some of the light emitters and the optical sensors are disabled while others remain active; and a battery power supply for powering the sensor module, wherein the light emitters and/or the optical sensors are dynamically directed in different directions;

wherein: the array of light emitters comprises a plurality of light emitters oriented in different directions such that the light emitters have different pointing vectors relative to each other, and the array of optical sensors comprises a plurality of optical sensors spatially distributed around the array of light emitters; or the array of optical sensors comprises a plurality of optical sensors oriented in different directions such that the optical sensors have different pointing vectors relative to each other, and the array of light emitters comprises a plurality of light emitters spatially distributed around the array of optical sensors; and wherein: the spatial distribution of the optical sensors around the array of light emitters includes the optical sensors forming a cross pattern around the array of light emitters or forming two lines of optical sensors above and below the array of light emitters; or the spatial distribution of the light emitters around the array of optical sensors includes the light emitters forming a cross pattern around the array of optical sensors or forming two lines of light emitters above and below the array of optical sensors.

27. A method for configuring an earbud, comprising:

assessing different combinations of light emitters and optical sensors to monitor vital signs of a user;

using one or more pairs of the light emitters and the optical sensors to determine the vital signs by assessing optical coupling between combinations of the light emitters and the optical sensors and deactivating the light emitters and the optical sensors based on the assessed optical coupling such that only some of the light emitters and the optical sensors are disabled while others remain active, wherein the light emitters and/or the optical sensors are dynamically directed in different directions wherein: the array of light emitters comprises a plurality of light emitters oriented in different directions such that the light emitters have different pointing vectors relative to each other, and the array of optical sensors comprises a plurality of optical sensors spatially distributed around the array of light emitters; or the array of optical sensors comprises a plurality of optical sensors oriented in different directions such that the optical sensors have different pointing vectors relative to each other, and the array of light emitters comprises a plurality of light emitters spatially distributed around the array of optical sensors; and wherein: the spatial distribution of the optical sensors around the array of light emitters includes the optical sensors forming a cross pattern around the array of light emitters or forming two lines of optical sensors above and below the array of light emitters; or the spatial distribution of the light emitters around the array of optical sensors includes the light emitters forming a cross pattern around the array of optical sensors or forming two lines of light emitters above and below the array of optical sensors.

* * * * *